United States Patent [19]

Gould et al.

[11] Patent Number: 4,810,543

[45] Date of Patent: Mar. 7, 1989

[54] ARTICLES HAVING LOW FRICTION SURFACES AND PRODUCTION THEREOF

[75] Inventors: Francis E. Gould; Charles K. Kliment, both of Princeton; George E. Seems, Pennington, all of N.J.

[73] Assignee: Tyndale Plains-Hunter Ltd., Princeton, N.J.

[21] Appl. No.: 920,232

[22] Filed: Oct. 17, 1986

[51] Int. Cl.$^4$ .................. B32B 27/00; B32B 7/04
[52] U.S. Cl. .................. 428/35.7; 128/348.1; 427/313.6; 428/403; 428/423.1; 428/420; 428/424.2; 428/36.8; 428/36.91; 521/53; 521/55; 521/176; 528/76; 528/36; 604/96; 604/264
[58] Field of Search .................. 427/393.6; 521/53, 55, 521/176; 528/76, 36; 604/96, 264; 128/348.1; 351/160 R; 428/420, 424.2, 403, 36

[56] References Cited

U.S. PATENT DOCUMENTS

| | | | |
|---|---|---|---|
| 3,975,350 | 8/1976 | Hudgin et al. | 521/158 |
| 4,156,066 | 5/1979 | Gould | 424/65 |
| 4,156,067 | 5/1979 | Gould | 522/65 |
| 4,459,317 | 7/1984 | Lambert | 428/423.1 |
| 4,487,808 | 12/1984 | Lambert | 428/423.1 |
| 4,589,873 | 5/1986 | Schwartz | 428/423.1 |
| 4,642,267 | 2/1987 | Creasy | 428/423.1 |
| 4,729,914 | 3/1988 | Kliment et al. | 428/423.1 |

*Primary Examiner*—Edith Buffalow
*Attorney, Agent, or Firm*—Ratner & Prestia

[57] ABSTRACT

The coefficient of friction of surfaces of articles, wherein the surface comprises a hydrophilic polyurethane polymer, is reduced by treating the surface with a mixture of concentrated sulfuric acid and a low molecular weight organic polyhydroxy compound, and removing excess treating mixture. Typical low friction articles produced thereby are boat hulls having drag resistant coatings, conduits having low friction linings, and cannula or body implants having slippery surfaces.

27 Claims, No Drawings

ARTICLES HAVING LOW FRICTION SURFACES AND PRODUCTION THEREOF

TECHNICAL FIELD

This invention relates to articles having low friction surfaces, that is, surfaces with a low coefficient of friction, and the process of achieving such result. More particularly, the invention pertains to such articles in which the low friction surfaces comprise a modified hydrophilic polyurethane polymer. The invention is also concerned with medical, veterinarian and biological uses of the articles as well as their application in hydrodynamics for providing improved liquid flow.

BACKGROUND OF THE INVENTION

There are numerous occasions, as in the practice of medicine and related arts, in which it is desirable to employ materials having a low coefficient of friction. For example, articles and devices such as contact lenses, catheters, peristaltic pumps, condoms, arteriovenous shunts, gastroenteric feed tubes and endotracheal tubes should be made of materials which have slippery surfaces when placed in contact with bodily fluids to facilitate insertion and removal of the articles from the body.

A class of materials which exhibit low friction properties, to a marked degree, are the hydrophilic polyurethane polymers described in U.S. Pat. Nos. 3,822,238 and 3,975,350. In the presence of an aqueous medium, these polymers absorb water with concomitant increase in volume and formation of a stable, water insoluble hydrogel distinguished by its very low coefficient of friction. Such polymers have found extensive usage in the manufacture of various types of body implants. Owing to the extremely slippery nature of the hydrogel or hydrated form of the polymer from which they are fabricated, the implants are readily inserted and removed from body tissues with minimal discomfort to the patient. Other important uses for the polyurethane polymers based on their low coefficient of friction are drag resistant surfaces such as coatings for boat hulls and the inner linings of conduits.

Another class of hydrophilic polyurethanes that form insoluble hydrogels is disclosed in U.S. Pat. Nos. 4,156,066 and 4,156,067. These polyurethanes are characterized by the presence of a lactone group in the polymer backbone. The lactone may be opened by hydrolytic cleavage to form a carboxylic acid which renders the polymer soluble in alkaline medium. Other specialized hydrophilic polyurethanes are the polyurethane diacrylates of U.S. Pat. No. 4,359,558, the polyurethane quaternary ammonium salts of U.S. Pat. No. 4,451,635 and the polyurethane polymers prepared from specific mixtures of alkylene glycols as described in commonly assigned U.S. patent application Ser. No. 879,156 filed June 6, 1986 now abandoned.

All of the above-cited U.S. patents and application are incorporated herein by reference as representative of the hydrophilic polyurethane polymers treatable in accordance with the present invention.

The hydrophilic character of the polyurethane polymers described in the cited patents is attributable to the presence of polar sites in the polymer backbone. In general, these are controlled by selecting the proper active hydrogen resin to be reacted with the polyisocyanate when carrying out the polyurethane synthesis. The polymers may be thermoplastic or thermosetting, depending on the degree of cross-linking. Difunctional reactants tend to give thermoplastic polymers whereas reactants of higher functionality tend to give thermoset polymers. By following the teachings of the patents, reactants can be selected to produce hydrophilic polyurethane polymers suitable for a variety of applications.

DESCRIPTION OF THE INVENTION

It has now been discovered that the coefficient of friction of articles made from hydrophilic polyurethane polymers of the above described types can be reduced even further by effecting certain modifications to the surface of said articles. The provision of the so-modified articles together with their preparation and uses is the principal object and purpose of the invention.

Broadly, the aforesaid object is implemented by providing, as an article of manufacture, a shaped body or substrate having a low friction surface produced by treating, for an effective period of time, a corresponding precursor surface of a hydrophilic polyurethane polymer on the substrate with a mixture of concentrated sulfuric acid and a low molecular weight organic polyhydroxy compound, and removing the treating mixture. In this specification, "concentrated" sulfuric acid means about 95–99 wt.% sulfuric acid. Commercial 98% sulfuric acid is preferred.

The substrate bearing the surface of hydrophilic polyurethane polymer can have any shape, both rigid and flexible, and can be formed of a wide variety of materials including the polyurethane polymer itself and composite materials. For substrates of materials different from the polyurethane polymer, the hydrophilic polyurethane polymer surface will normally be an upper or outer coating or layer applied to the substrate. Substrate materials commonly used as supports for the polymer coating are metal, glass, plastics, ceramics, rubber and rubbery polymers. Typical shapes are objects such as rods, films, tubes and pipes as well as complex shapes and devices. Generally speaking, the material and configuration of the substrate is governed by the particular manner in which the article of manufacture is to be employed.

Polymeric substrate materials are converted into a desired structure by conventional methods. Films may be formed by spreading solutions of the polymers on a suitable base and allowing the solvent to evaporate. The polymers may be placed in a mold of a desired configuration, heated and pressed into the desired structure. Tubing may be formed by heat extrusion methods. Desired structures may be provided with a coating of the polymers.

The quantities of concentrated sulfuric acid and low molecular weight polyhydroxy compound in the treating mixture can vary over wide limits. Normally, the mixture will contain on a 100% weight basis from about 50% to about 90% of concentrated sulfuric acid and from about 50% to about 10% of the polyhydroxy compound. Preferably, the solution contains about 80 parts of concentrated sulfuric acid and about 20 parts of the polyhydroxy compound.

The polyhydroxy compound must be at least partially soluble and stable in the concentrated sulfuric acid at the temperatures employed in treating the polymer surfaces. Generally, the treating temperatures can vary from about ambient up to about 60° C., preferably from about ambient to about 40° C. By the term "stable" is meant that the polyhydroxy compound is not decomposed or otherwise deleteriously affected by the concentrated sulfuric acid. For instance, many polyhydroxy compounds, notably the carbohydrates including sugars, starches and cellulose, tend to undergo dehydration with concomitant charring when contacted with concentrated sulfuric acid. Such polyhydroxy compounds are unsuitable for purposes of the invention. Preferably, the polyhydroxy compound used in the invention is a saturated, aliphatic compound of 2 to about 6 carbon atoms. More preferably, it should be a liquid which is miscible with sulfuric acid. The molecular weight of the hydroxy compounds will generally fall within a molecular weight range typified by polyols and polyol ethers such as ethylene glycol, diethylene glycol, triethylene glycol, glycerol, butanediols, trimethylene glycol, pentaerythritol, trimethylol propane, propylene glycol and the like, including any mixtures thereof, but higher molecular weights are acceptable provided the compounds have the requisite solubility and stability.

In preparing the treating solutions, considerable heat may be generated during mixing of the concentrated sulfuric acid and the polyhydroxy compound. Desirably, in order to avoid spattering or other adverse effects, mixing temperatures should not be allowed to rise above about 60° C. Cooling water can be applied to the mixing vessel to remove excess heat to prevent overheating.

Treatment of the hydrophilic polymer surface with the mixture of concentrated sulfuric acid and polyhydroxy compound is a critical operation in that the contact times are brief and must be carefully controlled. Otherwise, the polymer surface may be etched or eroded by the action of the concentrated acid, resulting in an increase rather than a decrease in surface friction. Of course, the period for effective treatment will vary depending on other factors as well (discussed below), such as temperature, concentration of the polyhydroxy compound in the acid solution, the composition of the hydrophilic polyurethane, and whether the hydrophilic polyurethane is in the dry or in the water swollen state.

Preferred hydrophilic polyurethane polymers herein are the polyurethanes described in the U.S. Patents and patent application cited above, having the property of absorbing water from an aqueous system with concomitant swelling and formation of an insoluble hydrogel. The higher the proportion of high molecular weight glycol used in forming the polyurethane polymer the shorter the period of contact required with the acid/polyhydroxy compound solution. For polymers made with low proportions of high molecular weight glycol, two periods of contact may be required. Where the proportion of high molecular weight glycols is low, a second period of contact with the acid/polyhydroxy compound solution may be required to obtain maximum slipperiness. Usually the hydrated polymer requires a shorter period of contact with the concentrated sulfuric acid solution than the dry form of the polymer. Apparently, the swollen surface allows faster penetration of the acid.

Another factor influencing the duration of treatment is the concentration of the low molecular weight polyhydroxy compound in the sulfuric acid. It has been determined that higher concentrations of polyhydroxy compound require longer periods of contact with the polymer surface.

In general, satisfactory results are realized by total contact times in the range of from about 2 seconds to about 30 seconds within the afore-specified temperature range. These parameters are readily determined by conducting a few test treatments on specimens of a particular hydrophilic polyurethane polymer using a test procedure such as ASTM-D-1894-75 for measuring static and kinetic coefficient of friction.

As indicated above, the hydrophilic polyurethane polymers disclosed in the cited patents and application are suitable in carrying out the invention. Preferably, the polyisocyanate used in preparing the polyurethanes is a diisocyanate or mixture of diisocyanates and the active hydrogen component is a mixture of a low molecular weight alkylene glycol such as diethylene glycol, a polyoxyethylene glycol having a number average molecular weight of from about 400 to about 20,000, and water. The NCO/OH ratio in the reaction mixture can vary from about 0.5/1 to about 1.0/1 while the percentage by weight of the alkylene glycol is no more than about 20% and the water content in the reaction mixture is no more than about 0.5%. An especially preferred polymer is produced by reacting on a 100% weight basis from about 12% to about 55% of methylenebis(cyclohexyl -4,4'-isocyanate), from about 2% to about 20% of the low molecular weight alkylene glycol such as diethylene glycol, from about 25% to about 85% of a polyoxyethylene glycol having a number average molecular weight of from about 1000 to about 8000 and from about 0.1% to about 0.5% water. The alkylene glycol may be the same or different from the polyhydroxy compound used in the treating solution for reducing the coefficient of friction as described above.

In addition to methylenebis(cyclohexyl-4,4'-isocyanate) other diisocyanates can be used in preparing suitable hydrophilic polyurethane polymers. These other diisocyanates include both aliphatic and aromatic types although the aliphatics are most preferred. Representative members are tetramethylene diisocyanate, hexamethylene diisocyanate, trimethylhexamethylene diisocyanate, cyclohexylene 1,2-diisocyanate, cyclohexylene 1,4-diisocyanate, and aromatic diisocyanates such as 2,4- and 2,6-tolylene diisocyanates. Also suitable are the isocyanate equivalents which form urethane linkages as exemplified by nitrile carbonates, such as adiponitrile carbonate of the formula:

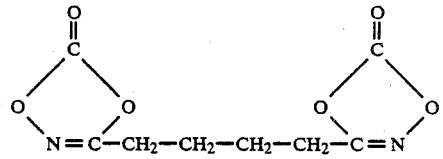

The alkylene glycols and polyoxyalkylene glycols are known entities which can be purchased from chemical supply houses. Typical commercial products are the polyoxyethylene glycols manufactured by the Union Carbide Corporation, under the trademark CARBOWAX®, of which CARBOWAX 1450, CARBOWAX 4500 and CARBOWAX 8000 are examples. The numbers refer to average molecular weights.

In preparing the hydrophilic polyurethane polymers, the glycol components and water are formed into a homogeneous mixture which is then reacted with the diisocyanate. The reaction is catalyzed by known catalysts, examples of which are tin salts and organic tin esters such as dibutyl tin dilaurate, tertiary amines such as triethyl diamine (DABCO), N,N,N',N'-tetramethyl- 1,3-butane diamine, and other recognized catalysts for urethane polymer synthesis.

The presence of water in the reaction mixture causes evolution of carbon dioxide, resulting in the polymer being obtained as a foam. This is an advantage in that the foamed polymer, owing to its large surface area, exhibits a high rate of dissolution, thereby facilitating the preparation of solutions of the polymer.

In adding the requisite quantity of water to the reaction mixture, allowance should be made for any moisture that may be present in the glycol components. It is not unusual for commercial grades of alkylene glycols and polyoxyalkylene glycols to contain varying amounts of water. Moreover, such glycols tend to be hygroscopic and even if free of water, may become contaminated with moisture from atmospheric exposure. Preferably, however, sufficient water will be present or added to cause foaming of the polyurethane polymer as it is formed. Generally, trace amounts up to about 0.5 parts by weight of water based on 100 parts by weight of the total reaction mixture will be effective, and for foaming, from about 0.1 to about 0.5 part by weight on the same basis.

The treated hydrophilic polyurethane polymer articles of the invention represent an advance over the corresponding untreated articles made from hydrophilic polyurethane polymers, particularly in applications where low surface friction is a desideratum, as in coatings, films, beads, controlled release systems, dentures, denture liners, dialysis membranes, burn dressings, contraceptive devices including condoms, sutures, surgical implants, cannula, blood oxygenators, intrauterine devices, vascular prostheses, oral delivery systems, eye bandages, corneal prostheses such as contact lens, gloves, surgical drapes and adhesives.

The invention is further illustrated by the following nonlimiting examples, in which all parts are by weight on a 100% basis unless otherwise indicated.

PREPARATION OF HYDROPHILIC POLYURETHAN POLYMERS

Polymer A

A homogenous melt was prepared by blending 55.5 parts CARBOWAX 1450, 8.8 parts of diethylene glycol and 0.3 parts of water, and heating the mixture to 65° C. To the resulting polyol mixture was added 35.4 parts of methylenebis(cyclohexyl-4,4'-isocyanate), a product sold as DESMODUR W ® by Mobay Chemical Corporation, Pittsburgh, PA, with constant stirring. Next, 0.2 parts of stannous octoate catalyst was added. The mixture exothermed in about one minute. When the temperature reached 70° C., the mixture was poured into a polypropylene tray and placed in a circulating oven and allowed to cure at 100° C. for one hour. The resulting foamed polymer, on hydration to equilibrium, gave a hydrophilic polyurethane polymer having a water content of 60%.

Polymer B

Following the procedure for Polymer A, a hydrophilic polyurethane polymer was prepared from 84.8 parts of CARBOWAX 8000, 2.4 parts of diethylene glycol, 0.4 parts of water, 12.3 parts of DESMODUR W and 0.15 parts of dibutyl tin dilaurate. The so-obtained hard, foamed polymer, on hydration to equilibrium, had a water content of 32%.

Polymer C

Following the procedure for Polymer A, another hydrophilic polyurethane polymer was prepared from 50.1 parts of CARBOWAX 1450, 10.8 parts of diethylene glycol, 0.2 parts of water and 30.8 parts of DESMODUR W. The resulting foamed polymer, on hydration to equilibrium, had a water content of 51%.

PRODUCTION OF LOW SURFACE FRICTION ARTICLES

Example 1

A tube, formed into a Foley urinary catheter from a rubber latex, was dip coated with a solution prepared by dissolving 4 parts of Polymer A in a mixture of 92 parts of ethyl alcohol and 4 parts of water. The coating was air dried and then cured at 60° C. for 10 minutes.

After hydrating the polymer coating to equilibrium, the catheter was immersed for 10 seconds in a solution of 80 parts of 98% sulfuric acid and 20 parts of glycerol prepared by mixing the ingredients at ambient temperature. The catheter was immediately withdrawn from the treating bath and washed thoroughly with water until all traces of the acidic solution were removed.

The uncoated tubing had static and kinetic coefficients of friction (as measured by ASTM-D-1894-75) of 0.37 and 0.42, respectively. The coefficients of friction for the coated tubing were 0.18 and 0.4 while those of the sulfuric acid-glycerol treated coating were 0.22 and 0.12.

Example 2

A specimen of tube substantially equivalent to that of Example 1 was coated, using a solution prepared by dissolving 3 parts of Polymer B in 97 parts of dichloromethane. The tube was dipped in the solution, air dried, dipped again, air dried and cured at 80° C. for 10 minutes.

The coated tube was immersed in a sulfuric acid-glycerol solution as in Example 1, only this time the time of immersion was shortened to 4 seconds. The tube was immediately washed free of treating solution and its slipperiness measured. While the tube coated with the hydrophilic polymer alone had static and kinetic coefficients of friction of 0.04 and 0.04, respectively, after the slippery treatment these fell to 0.02 and 0.01.

The coating with the slippery treatment remains flexible, its swelling and deswelling (drying) is fully reproducible, and it is not eluted by low molecular compounds even after prolonged extraction.

Example 3

Polymer C was granulated to particles ¼-inch in diameter and dissolved in chloroform to a 10% solids solution. The resulting clear solution was cast on release paper, using a doctor blade. Following drying at ambient temperature in a well ventilated hood, a film was obtained having a thickness of 0.2 mm.

The film was hydrated in water for three hours. A solution, prepared from 60 parts of sulfuric acid (98%) and 40 parts of ethylene glycol, was heated to 40° C. The hydrated film was immersed in the acid solution for 15 seconds, removed, washed with water, and reimmersed in the acid solution for an additional 10 seconds. Following a thorough wash in water, a film with a highly slippery surface resulted.

Example 4

Polymer B was granulated and then fed into a one-inch vented Killion extruder. A tube having an ID of 8 mm and OD of 10 mm was extruded. The tube was hydrated in water and its inner wall treated with a solution of 75 parts of 98% sulfuric acid and 25 parts of propylene glycol at ambient temperature for 20 seconds by passing the mixture through the tube at a rate which gave the above quoted contact time. The tube was washed well with water to remove the acid solution.

The inner slippery layer prevented the onset of turbulence and thus allowed for a greater flow of aqueous liquid through the tube. This phenomenon was measured by connecting 1 m length of the hydrated tube to a water faucet, running the water through the tube for a fixed time period and collecting the water. The same experiment was repeated with an identical tube, but which had not received the slippery treatment. The water flow through the treated tube was found to be 22% higher than through the untreated tube.

Example 5—Comparative

Structures formed of a conventional hydrophobic polyester polyurethane polymer were treated with an acid-glycerol solution as in Example 1 for periods of 2 seconds to 3 minutes followed by water washing and repetition of the procedure. The surfaces become roughened and were not slippery. Nylon and polypropylene tubing were treated similarly with like results.

We claim:

1. As an article of manufacture, a shaped substrate having a low friction surface produced by treating, for an effective period of time, a corresponding precursor surface of a hydrophilic polyurethane polymer on the said substrate with a mixture of concentrated sulfuric acid and a low molecular weight polyhydroxy compound, and removing excess mixture.

2. The article of manufacture according to claim 1 wherein the substrate is a film.

3. The article of manufacture according to claim 2 wherein the film is in the form of a glove.

4. The article of manufacture according to claim 2 wherein the film is in the form of a denture or denture liner.

5. The article of manufacture according to claim 2 wherein the film is in the form of a condom.

6. The article of manufacture according to claim 1 wherein the substrate is a contact lens.

7. The article of manufacture according to claim 1 wherein the substrate is an extruded shape.

8. The article of manufacture according to claim 1 wherein the substrate is a tube.

9. The article of manufacture according to claim 1 wherein the substrate is a bead.

10. The article of manufacture according to claim 1 wherein the substrate is an intravenous catheter.

11. The article of manufacture according to claim 1 wherein the substrate is a cannulae.

12. The article of manufacture according to claim 1 wherein the substrate is an intrauterine device.

13. The article of manufacture according to claim 1 wherein the substrate is a body implant.

14. An article of manufacture as in claim 1 wherein the hydrophilic polyurethane polymer comprises the reaction product of a mixture of an organic diisocyanate, a low molecular weight alkylene glycol, a polyoxyethylene glycol having a number average molecular weight of from about 400 to about 20,000, and water, the said reaction mixture having an NCO/OH ratio of from about 0.5/1 to about 1.0/1, and wherein the percent by weight in the reaction mixture of the low molecular weight alkylene glycol is no more than about 20% and the water content is no more than about 0.5%.

15. An article of manufacture as in claim 1 wherein the hydrophilic polyurethane polymer comprises the reaction product of a mixture on a 100% weight basis, of from about 12% to about 55% of methylenebis(cyclohexyl-4,4'-isocyanate), from about 2% to about 20% of a low molecular weight alkylene glycol, from about 25% to about 85% of a polyoxyethylene glycol having a number average molecular weight of from about 1000 to about 8000, and from about 0.1% to about 0.5% water.

16. The article of manufacture according to claim 1 wherein the hydrophilic polyurethane polymer surface comprises the surface of a hydrophilic polyurethane coating on the substrate.

17. The article of manufacture according to claim 16 wherein the substrate is a flexible substrate.

18. The article according to claim 17 wherein the flexible substrate rubber.

19. The article according to claim 1 wherein the mixture comprises a solution containing on a 100% weight basis from about 10 to about 50 parts of the low molecular weight polyhydroxy compound and from about 50 parts to about 90 parts of concentrated sulfuric acid.

20. The article according to claim 19 wherein the polyhydroxy compound is selected from ethylene glycol, diethylene glycol, triethylene glycol, glycerol, butanediol, trimethylene glycol, pentaethritol, trimethylol propane and propylene glycol, and the concentration of the sulfuric acid is about 98%.

21. The article according to claim 1 wherein the treatment period is from about 2 to 30 seconds.

22. A process for reducing the coefficient of friction of the surface of an article, said surface comprising a hydrophilic polyurethane polymer, said process comprising treating the surface with a mixture of concentrated sulfuric acid and a low molecular weight polyhydroxy compound for an effective time, and removing excess mixture.

23. The process of claim 22 wherein the hydrophilic polyurethane polymer comprises the reaction product of a mixture of an organic diisocyanate, a low molecular weight alkylene glycol, a polyoxyethylene glycol having a number average molecular weight of from about 400 to about 20,000, and water, the said reaction mixture having an NCO/OH ratio of from about 0.5/1 to about 1.0/1, and wherein the percent by weight in the reaction mixture of the low molecular weight alkylene glycol is no more than about 20% and the water content is no more than about 0.5%.

24. The process of claim 22 wherein the hydrophilic polyurethane polymer comprises the reaction product of a mixture of on a 100% weight basis, of from about 12% to about 55% of methylenebis(cyclohexyl-4,4'-isocyanate), from about 2% to about 20% of a low molecular weight alkylene glycol, from about 25% to about 85% of a polyoxyethylene glycol having a number average molecular weight of from about 1000 to about 8000, and from about 0.1% to about 0.5% water.

25. The process of claim 22 wherein the treating mixture comprises a solution containing on a 100% weight basis from about 10 to about 50 parts of the low molecular weight polyhydroxy compound and from about 50 parts to about 90 parts of concentrated sulfuric acid.

26. The process of claim 25 wherein the polyhydroxy compound is selected from ethylene glycol, diethylene glycol, triethylene glycol, glycerol, butanediol, trimethylene glycol, pentaethritol, trimethylol propane and propylene glycol, and the concentration of the sulfuric acid is about 98%.

27. The process of claim 22 wherein the time of treatment is from about 2 to 30 seconds.

* * * * *